United States Patent [19]

Bercu

[11] Patent Number: 4,844,096

[45] Date of Patent: Jul. 4, 1989

[54] METHOD OF DIAGNOSING GROWTH HORMONE DISORDERS EMPLOYING SOMATOSTATIN INFUSION

[75] Inventor: Barry B. Bercu, Tampa, Fla.

[73] Assignee: University of South Florida, Tampa, Fla.

[21] Appl. No.: 174,578

[22] Filed: Mar. 29, 1988

[51] Int. Cl.$^4$ ............................................. A61B 5/00
[52] U.S. Cl. ................................... 128/630; 128/632; 424/9
[58] Field of Search ................... 128/630, 632; 424/9

[56] References Cited

U.S. PATENT DOCUMENTS

| | | | |
|---|---|---|---|
| 4,410,512 | 10/1983 | Bowers | 514/17 |
| 4,410,513 | 10/1983 | Momann | 514/17 |
| 4,411,890 | 10/1983 | Momann | 514/17 |

OTHER PUBLICATIONS

Catt, An ABC of Endocrinology, Little Brown and Company, Boston, 1971, pp. 30–34.
Harrison's Principles of Internal Medicine, 10th Ed., McGraw-Hill, N.Y., 1983, pp. 597, 598 and 589.

Primary Examiner—Kyle L. Howell
Assistant Examiner—John C. Hanley
Attorney, Agent, or Firm—Ronald E. Smith; Joseph C. Mason, Jr.

[57] ABSTRACT

A diagnostic method whereby the sensitivity of inhibition of nocturnal growth hormone secretion by a growth hormone inhibiting factor is tested. The inhibiting factor or hormone, somatostatin is introduced into the bloodstream of sleeping children with classical GH deficiency, growth hormone neurosecretory dysfunction, and related disorders. The degree of suppression of the growth hormone secretion is studied to diagnose each child's condition preparatory to beginning a treatment program.

11 Claims, No Drawings

METHOD OF DIAGNOSING GROWTH HORMONE DISORDERS EMPLOYING SOMATOSTATIN INFUSION

BACKGROUND OF THE INVENTION

1. Field of the Invention

This invention relates, generally, to diagnostic tests having utility in connection with the study of growth hormone disorders. More particularly, it relates to the use of somatostatin as a diagnostic test where the degree of growth hormone suppression is observed.

2. Description of the Prior Art

Human growth is believed to be regulated, at least in part, by a hormone secreted by the pituitary gland; the hormone has been identified and is known as the growth hormone. The normal endogenous secretion of growth hormone is dependent upon the interplay of growth hormone releasing factor and somatostatin. The components of this system are the hypothalamic-pituitary axis and the higher brain centers of the central nervous system.

Accordingly, dysfunction of the pituitary gland, at least in relation to its secretion of the growth hormone, may be responsible for dwarfism and gigantism as well.

There are known methods whereby growth hormone secretion by the pituitary gland can be provoked. Prior to the present invention, diagnosis of a child of unusually short stature included provoking said secretion, observing the results and little more.

This prior art procedure of employing provocation as a diagnostic tool, while having utility, requires improvement. There are many types of growth hormone disorders, and there is a need for a more powerful diagnostic tool to aid the physician. The provocative test itself, standing alone, does not suggest any further procedures that could substantially enhance the specificity of the diagnosis.

Moreover, the definition of growth hormone deficiency based on provocative testing of growth hormone secretion may not accurately reflect the total endogenous output of growth hormone secretion.

For example, where less than 10 ng/mL (nanograms per milliliter) of the growth hormone is secreted after two or more provocative tests, a diagnosis of classical growth hormone deficiency may be in order, in accordance with prior art teachings. Where greater than 10 ng/mL of growth hormone are secreted after two or more provocative tests but where the concentration during a 24 hour study is low (blood sampling every 20 minutes), a diagnosis of growth hormone neurosecretory dysfunction may be in order. Other responses can lead to a diagnosis of hypersomatotropism.

The hormone somatostatin (sold under the trademark Stilamin and manufactured by Serono Laboratories, Inc.) and its analogs or chemical equivalents, is known to inhibit the secretion of growth hormone. Theoretically, it could be used in the treatment of gigantism. Heretofore, no known diagnostic procedure relating to growth dysfunction had employed somatotatin as a diagnostic tool.

SUMMARY OF THE INVENTION

Somatostatin, a known inhibitor of growth hormone, is used as a diagnostic probe to examine the inhibitory regulation in disorders of growth hormone (GH) neurosecretion.

More particularly, it is infused intravenously at a low dose at an acute rate during the time the patient is sleeping, thereby effectively blocking the largest nocturnal pulses of growth hormone. Different patients having differing dysfunctions are diagnosed by the differing responses to the application of the inhibitor.

DETAILED DESCRIPTION OF A PREFERRED EMBODIMENT

Growth hormone secretion is probably under the dual control of growth hormone releasing hormone (GHRH) and growth hormone inhibiting factor (somatostatin). In children having growth hormone-neurosecretory dysfunction and/or GH deficiency, there may be an underproduction of GHRH, an overproduction of the inhibiting hormone, somatostatin, or both.

Prior to treating a patient with classical growth hormone deficiency, or a related disorder, the present inventor believes it is helpful to know what growth hormone reserves are in the pituitary gland. However, heretofore there have been no completely satisfactory diagnostic tests for determining the patient's pituitary growth hormone reserves after inhibition of growth hormone secretion.

Studies have shown that most growth hormone secretion occurs when a child is sleeping, because that is when the pituitary gland is most active. Nocturnal secretion of the growth hormone occurs at least to some extent in even the most severe cases of growth hormone deficiencies.

The utility of somatostatin (a 14 amino acid peptide) and its chemical equivalents as a diagnostic tool to assess pituitary GH reserve and the role of endogenous growth hormone releasing hormone (GHRH) is now disclosed.

In a preliminary study, seven children were selected for assessment. Five of the children were given an intravenous bolus of somatostatin at night, as soon as sleep commenced; the infusion continued, uninterrupted, for six hours. This six hour interval was selected because said interval of time is sufficiently long to block the largest nocturnal GH pulses. The dose for the somatostatin was 1.5 $\mu g/kg$ (micrograms per kilogram) intravenous bolus followed by infusion at 1.5 $\mu g/kg/hr$. The other two children received the same treatment during their wakeful state.

In three children, diagnosed as having classical GH deficiency (peak GH less than 10 ng/mL) after provocative testing and reduced mean 24 hour GH concentration of 1.2, 1.7, 0.8 ng/mL, the low basal level of GH (about 2.1, 1.4, 0.6 ng/mL) increased slightly after the child went to sleep. It was observed that, for these three children, the GH concentrations were not suppressed.

Peak GH levels one or more hours after starting the somatostatin infusion were 2.7, 2.5, 2.4 ng/mL. There was no change in prolactin (PRL) secretion whereas insulin values declined.

In two children with GH neurosecretory dysfunction (GHND), i.e., normal GH provocative tests with peak less than 10 ng/mL and reduced mean 24 h GH concentration 1.5, 1.8 ng/mL, the somatostatin suppressed basal nocturnal GH secretion to less than 0.5 ng/mL after an initial GH pulse. PRL was not suppressed by the somatostatin.

In a patient with hypersomatotropism, the somatostatin reduced GH from 42 ng/mL to a nadir of 20.6 ng/mL and PRL from 78 ng/mL to a nadir of 49 mg/mL. Unlike the GH deficient and GHND patients, there was a significant rebound of GH and PRL one hour following withdrawal of the somatostatin. One month after hypophysectomy, basal GH (about 2.0 ng/mL) was not further suppressed by somatostatin. In a child with diabetes mellitus, GH secretion was suppressed to less than 0.5 ng/mL following somatostatin.

From these data, it is clear that somatostatin responsitivity differs between patients having classical GH deficiency and GH neursecretory dysfunction. This suggests that somatostatin has a role in GH neurosecretory abnormalities. Moreover, in treated acromegaly, there is a lack of somatostatin-induced GH suppression which suggests residual autonomously secreting somatotrophs. Thus, the preliminary study suggested an abnormal role for somatostatin but did not exclude GHRH in the regulation of GH secretion in these pathological states.

In a more comprehensive study, a larger group of children having differing GH secretory disorders was tested to determine whether they would respond differently to intravenous infusion of somatostatin. Depending upon the different responses, if any, it was believed that the dynamics of pituitary growth hormone reserves of each child could be assessed. Treatment, accordingly, could be adapted to fit the individual child.

Children known to have GH deficiency were placed in a first group; those having GH-neurosecretory dysfunction were placed in a second group; those having a short stature and suspected of having a GH dysfunction were placed in a third group and central nervous system irradiated children suspected of having said dysfunction were placed in a fourth group. As in the preliminary study, each child was given an intravenous bolus of somatostatin at night, as soon as sleep commenced; the infusions continued, uninterrupted, for six hours. As in the preliminary study, the rate of infusion was 1.5 $\mu$g/kg/hr.

For each child, baseline samples were taken when he or she first began sleeping and additional samples were taken every 20 minutes thereafter for seven hours.

The degree of suppression of GH secretion was observed as it was felt that the amount of suppression experienced by each child might differ and that the individual response would be helpful as a diagnostic tool. It was also believed that the recovery or rebound rate of GH secretions would aid the diagnosis as well, as a secondary factor to consider after the degree of suppression.

Moreover, it was believed that the dosage of 1.5$\mu$g/kg could be excessive in that perhaps all patients would experience the same degree of suppression and exhibit substantially the same rebound in GH levels after the treatment. The dosage would then be decreased until differences began appearing, if they ever were to appear.

However, it was learned that the 1.5 $\mu$g/kg/hr was not excessive. Subsequently, the dose was increased to 2.5 $\mu$g/kg/hr and beyond.

Statistically significant differences in the degree of suppression and rebound rates were discovered.

This important breakthrough advances medical technology in a pioneering manner, and for that reason the claims which follow are to be interpreted in a broad manner, as a matter of law.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

Now that the invention has been described,

What is claimed is:

1. A method for diagnosing pituitary growth hormone deficiency or neurosecretory dysfunction in an individual comprising the steps of:
   introducing a predetermined amount of somatostatin at a predetermined rate into the bloodstream of an individual for a predetermined period of time, measuring any suppression of growth hormone in said individual, determining if growth hormone deficiency or neurosecretory dysfunction exists in the individual from any measured suppression.

2. The method of claim 1, further comprising the step of introducing said predetermined amount of somatostatin at a rate of 1.5 $\mu$g/kg/hr for a period of six hours.

3. The method of claim 2, wherein said predetermined amount of somatostatin is 1.5 $\mu$g/kg.

4. The method of claim 3, further comprising the step of introducing said somatostatin while said individual is sleeping.

5. The method of claim 3, further comprising the step of measuring the percentage of suppression of growth hormone in said individual.

6. The method of claim 5, further comprising the step of measuring the rebound rate of growth hormone in said individual.

7. The method of claim 1, further comprising the step of introducing said predetermined amount of somatostatin at a rate of 2.5 $\mu$g/kg/hr for a period of six hours.

8. The method of claim 7, wherein said predetermined amount of somatostatin is 2.5 $\mu$g/kg.

9. The method of claim 8, further comprising the step of introducing said somatostatin while said individual is sleeping.

10. The method of claim 8, further comprising the step of measuring the percentage of suppression of growth hormone in said individual.

11. The method of claim 10, further comprising the step of measuring the rebound rate of growth hormone in said individual.

* * * * *